United States Patent [19]

Engelbrecht

[11] 4,232,120

[45] Nov. 4, 1980

[54] INSTRUMENT AND METHOD FOR TRANSFERRING MICROBIOLOGICAL SAMPLES IN A PREDETERMINATED GASEOUS ENVIRONMENT

[76] Inventor: Eduard Engelbrecht, Park Vronesteyn 49, Voorburg, Netherlands

[21] Appl. No.: 5,348

[22] Filed: Jan. 22, 1979

[30] Foreign Application Priority Data

Feb. 2, 1978 [CH] Switzerland .................. 1129/78

[51] Int. Cl.$^3$ .............................................. C12Q 1/24
[52] U.S. Cl. ...................................... 435/30; 435/292; 435/294; 435/311; 435/313; 435/801
[58] Field of Search ................ 435/30, 243, 261, 292, 435/293, 294, 311, 313, 317, 818, 801

[56] References Cited

U.S. PATENT DOCUMENTS

| | | | |
|---|---|---|---|
| 3,666,629 | 5/1972 | Moore | 435/30 X |
| 3,734,358 | 5/1973 | Bergeron | 435/30 |
| 3,772,154 | 11/1973 | Isenberg et al. | 435/30 X |
| 3,778,351 | 12/1973 | Rosov | 435/30 X |
| 4,015,942 | 4/1977 | Coupe | 435/292 X |

OTHER PUBLICATIONS

Baillie et al., "Automation, Mechanization & Data Handling in Microbiology" Academic Press (1970) pp. 180–182.

*Primary Examiner*—R. B. Penland
*Attorney, Agent, or Firm*—Kurt Kelman

[57] ABSTRACT

While transferring a portion of a microbiological culture medium from one receptacle to another by means of a needle disposed on a base, a flow of gas is directed from the base towards the needle to form a protective gaseous environment around the transferred culture medium portion.

**9 Cla

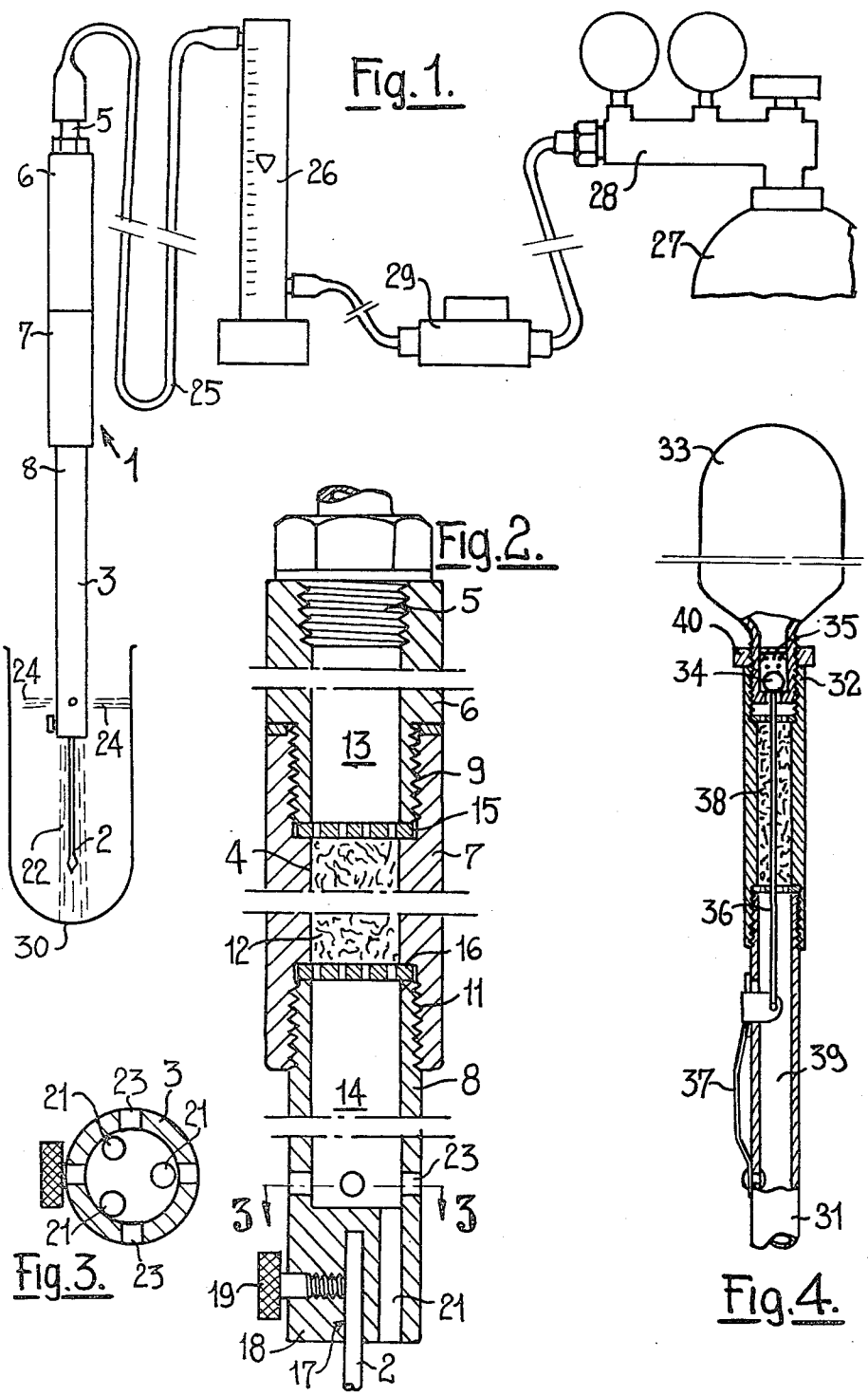

INSTRUMENT AND METHOD FOR TRANSFERRING MICROBIOLOGICAL SAMPLES IN A PREDETERMINATED GASEOUS ENVIRONMENT

The present invention relates to apparatus and a method for inoculating or transferring microbiological cultures.

Stocks of bacteria are frequently cultured for medical or industrial purposes. Certain ones of these stocks require for survival and development a particular environment, especially as far as the ambient atmosphere is concerned. For example, certain stocks of bacteria are killed by the oxygen in the air. Therefore, while these bacterial cultures are transferred, particularly during inoculation, it is absolutely necessary to maintain a predetermined atmosphere around the transferred material.

For this purpose, it has been proposed to use a fluid-tight handling chamber with a transparent wall and defining ports with gloves which permit an operator to manipulate instruments in the interior of the chamber. The chamber operates as a lock chamber and has means for control of its atmosphere.

Operating in such a chamber from the outside is rather difficult. Furthermore, since the instruments must frequently be sterilized by heat, an electric heater must be mounted inside the chamber and this constitutes a source of heat which, in turn, requires cooling means or means for regenerating the atmosphere.

It has also been proposed to make use of an installation with tubes directed to the culture medium and permitting the latter to be immersed in the desired atmosphere. But since it is necessary to provide a sufficient working space between the tubes and the culture medium, the protective gas also entrains ambient air, particularly in view of the turbulences due to the presence of the instruments in this working space.

Furthermore, while the sample is transferred from one receptacle to another, it is exposed to the ambient atmosphere.

It is the primary object of this invention to overcome these disadvantages and difficulties, and to enable the culture transfer to be effected in a desired atmosphere without recourse to fluid-tight operating chambers and to maintain the transferred sample in a protective gaseous environment during the entire transfer procedure from one receptacle to another.

The above and other objects are accomplished according to the invention with an apparatus which comprises a needle for successively introducing a portion of a culture into different receptacles to transfer the culture from one receptacle to another receptacle, as base on which the needle is disposed and wherefrom it protrudes, and distributing means carried by the base and operable to direct a flow of gas along the needle to form a protective gaseous environment around the transferred portion of the culture.

In accordance with another aspect of the present invention, microbiological cultures are inoculated or transferred by successively removing a portion of a culture from one receptacle by means of a needle disposed on a base, which includes the step of retracting the needle with the removed culture portion on an end of the needle from the one receptacle, and introducing the removed culture portion on the end of the needle into another receptacle to transfer the culture portion thereto, and directing a flow of gas from the base along the needle to provide a protective gaseous environment around the transferred portion of the culture while the needle is retracted from the one receptacle and the removed culture medium portion is introduced into the other receptacle.

The above and other objects, advantages and features of this invention will become more apparent from the following detailed description of certain now preferred embodiments thereof, taken in conjunction with the accompanying drawing wherein FIG. 1 is a schematic side elevational view of an apparatus according to the invention;

FIG. 2 is a fragmentary longitudinal section, on an enlarged scale, of a portion of the apparatus;

FIG. 3 is a section along line 3—3 of FIG. 2; and

FIG. 4 is an axial section of a modified portion of the apparatus.

Referring now to the drawing and first to FIG. 1, the illustrated apparatus is shown to comprise hand-held instrument 1 which includes needle 2 disposed at a forward end of base 3. One form of this base is illustrated in FIG. 2 where it is shown to be constituted by hollow box 4 having inlet connection 5 at a rear end of the box.

Illustrated box 4 is formed of three readily detachable parts 6, 7 and 8 which are assembled by threaded connections 9 and 11. Filter 12 is mounted in box 4 and is arranged between front chamber 14 and rear chamber 13 which is in communication with inlet connection 5 so that the filter is traversed by gas coming from the inlet connection. The filter is constituted by a removable filter unit disposed between two perforated disc 15 and 16 held in place between shoulders on center part 7 and the interior ends of parts 8 and 9 when the parts are screwed together.

The inner end of needle 2 is positioned in axial bore 17 in front end 18 of the base and retained therein by set screw 19.

As shown in FIGS. 2 and 3, distributing means is carried by base 3 and is operable to direct a flow of gas along needle 2 to form a protective gaseous environment around the transferred portion of the culture when the apparatus 1 is in use for inoculating or transferring microbiological cultures. The illustrated distributing means comprises a principal nozzle operable to expel the gas forwardly in a direction substantially parallel to needle 2, the nozzle being constituted by three longitudinal ducts 21 in front section 18 of the base around the rear end of the needle to produce a gas flow 22 substantially parallel to the needle, as shown in FIG. 1. An auxiliary nozzle is operable to expel a flow of gas 24 laterally at the rear end of the needle and is comprised of four radial ducts 23 in front end 18 of the base and positioned slightly behind the rear end of the needle (FIG. 2).

A source of protective gas under pressure comprises a flask 27 holding the gas under pressure and having an output connected to a group of gas pressure regulators 28 in turn connected to valve 29 which may be push-controlled, for instance by a foot pedal, the output of the valve being connected to a gas flow meter 26. A flexible gas feed pipe 25 connects inlet connection 5 to the flow meter.

When the cock of the pressure regulator 28 is open and valve 29 is operated, the gas from flask 27 will enter into hollow base 3 through inlet connection 5, the flow of the gas being indicated by flow meter 26 and being capable of being controlled by the pressure regulator. After the gas has traversed filter 12, it enters front chamber 14 whence it escapes in the form of an axial flow 22 and a lateral or radial flow 24 through ducts 21 and 23, respectively. These ducts serve as gas distributors assuring a protective gaseous environment around needle 2.

In operating the illustrated apparatus for inoculating or transferring microbiological cultures, a portion of a culture is first removed from one receptacle 30 by means of needle 2 disposed on base 3, which includes the step of retracting the needle with the removed culture portion on an end of the needle from receptacle 30, and then introducing the removed culture portion on the end of the needle into another receptacle (not shown) to transfer the culture portion thereto, hand-held instrument 1 simply being moved from the one to the other receptacle. While needle 2 is retracted from receptacle 30 and the removed culture portion is introduced into the other receptacle, flow of gas 22 is directed from base 3 along needle 2 to provide a protective gaseous environment around the transferred portion of the culture. At the same time, the gas escaping through lateral ducts 23 removes the air contained in receptacle 30. While the needle is retracted, the removed sample remains securely protected by gas curtain 22. The needle is then immersed into a second receptacle where the inoculation with the culture takes place still under the protection of principal gas flow 22 while auxiliary gas flow 24 also fills the second receptacle with the protective gas. In this manner, the inoculum remains protected during the entire transfer.

In the modified base shown in FIG. 4, elongated hollow sleeve 31 constitutes the base on which needle 2 is disposed and the sleeve has inlet connection 32 for the gas. Gas feed cartridge 33 containing the protective gas under pressure is detachably connected to inlet connection 32 by a threaded joint. Ball valve 34 retains the gas under pressure in the cartridge, the ball of the valve being held in the closing position by compression spring 35. A valve operating element constituted by push rod 36 is mounted in the interior of hollow sleeve 31 and exterior control member 37 constituted by a deformable hand lever operates push rod 36 to open the valve by axially moving the push rod against the ball of the valve and to permit gas under pressure to enter from cartridge 33 into hollow sleeve 31. The gas traverses filter 38 and enters into front chamber 39 of sleeve 31 whence it escapes through nozzle ducts in the same manner as described in connection with FIGS. 2 and 3.

The position of cartridge 33 on inlet connection 32 may be controlled by nut 40 to regulate the maximum opening of the valve and the resultant gas flow.

Obviously, the needle and the gas nozzles providing the protective gas flow around the needle may take various forms and, if desired, the base on which the needle is disposed may be part of a portable tool, such as a robot.

What is claimed is:

1. An apparatus for transferring or inoculating microbiological cultures requiring a protective gaseous environment during handling and incubation, which comprises
    (a) a needle arranged to be successively introduced into different receptacles to transfer a portion of microbiological culture carried by the needle from one receptacle to another receptacle;
    (b) a hollow base means on which the needle is disposed; and
    (d) gas distributing means comprising a nozzle carried by the base and operable to direct a flow of gas substantially parallel to, and around, the needle to form the gaseous environment as a protective shield between the portion of the microbiological culture carried by the needle and the ambient atmosphere.

2. The apparatus of claim 1, wherein the gas distributing means comprises a nozzle operable to expel the flow of gas substantially parallel to, and around, the needle, the nozzle being located in relation to the needle so that the flow of gas is spaced sufficiently from the needle to avoid any direct pressure of the gas flow on the microbiological culture portion carried by the needle sufficient to dislodge the culture portion from the needle.

3. The apparatus of claim 2, wherein the nozzle is constituted by several longitudinal ducts in the base in a circular arrangement around the needle, the ducts having axes extending substantially parallel to the axis of the needle.

4. The apparatus of claim 2, wherein the gas distributing means further comprises an auxiliary nozzle disposed close to the base and operable to expel the gas laterally with respect to the axis of the needle.

5. The apparatus of claim 1, wherein the hollow base means is constituted by a hollow shaft having an outlet end on which the base is mounted, and further comprising a source of the gas connected to an inlet end of the hollow shaft for supplying the gas to the gas distributing means through the interior of the hollow shaft.

6. The apparatus of claim 5, further comprising a filter mounted in the interior of the hollow shaft and arranged to be traversed by the gas flowing therethrough to the gas distributing means, the hollow shaft being constituted by readily detachable tubes whereby the filter may be replaced on detachment of the tubes.

7. The apparatus of claim 5, wherein the source of the gas is a gas feed cartridge containing the gas under pressure and having a valve for retaining the gas in the cartridge, and further comprising a valve operating element mounted in the interior of the hollow shaft and an exterior control member for operating the valve operating element to allow a predetermined amount of the gas to flow from the cartridge through the interior of the hollow shaft to the gas distributing means.

8. The apparatus of claim 1, further comprising means for controlling the flow rate of the gas from the gas distributing means.

9. A method for transferring or inoculating microbiological cultures requiring a protective gaseous environment during handling and incubation, which consists essentially of the steps of
    (a) removing a portion of a microbiological culture from a receptacle by a needle carrying the culture portion mounted on a hollow base, the needle carrying the culture portion being retracted from the receptacle to remove the portion;
    (b) isolating the removed microbiological culture portion carried by the needle from the ambient atmosphere by causing a protective gas to flow from the hollow base substantially parallel to, and around, the needle to form a protective gaseous environment between the culture portion and the ambient atmosphere, the gas flow being controlled to avoid any direct pressure on the culture portion sufficient to dislodge the culture portion from the needle;

(c) moving the needle to another receptacle while maintaining the gas flow as a protective shield;

(d) introducing the needle into the other receptacle and inoculating a culture medium in the other receptacle with the removed culture portion carried by the needle;

(e) simultaneously establishing the protective gaseous environment in the other receptacle by causing the gas flow to expel the air initially present in the other receptacle therefrom;

(f) retracting the needle from the other receptacle; and (g) hermetically sealing the other receptacle from the ambient atmosphere so as to maintain the gaseous environment in the other receptacle whereby continuous shielding of the inoculating microbiological culture from the ambient atmosphere is obtained.

* * * * *